United States Patent [19]

Pollock et al.

[11] Patent Number: 4,725,576
[45] Date of Patent: Feb. 16, 1988

[54] FUNGICIDAL POLYPEPTIDE COMPOSITIONS CONTAINING L-HISTIDINE AND METHODS FOR USE THEREFORE

[75] Inventors: Jerry J. Pollock, Nesconset, N.Y.; Bruce J. MacKay, Somerville, N.J.

[73] Assignee: Research Foundation of State University of New York, Albany, N.Y.

[21] Appl. No.: 778,490

[22] Filed: Sep. 20, 1985

Related U.S. Application Data

[63] Continuation-in-part of Ser. No. 566,515, Dec. 29, 1983, abandoned.

[51] Int. Cl.⁴ .................. A61K 37/02; A61K 7/16
[52] U.S. Cl. .......................... 514/2; 514/967; 514/968; 514/21; 424/54
[58] Field of Search ............... 514/2, 967-968, 514/12-18, 21; 424/54

[56] References Cited

U.S. PATENT DOCUMENTS 3,497,591  2/1970  Yankell et al. ................. 424/54
4,154,813  5/1979  Kleinberg .......................... 424/54

OTHER PUBLICATIONS

Baum et al., Arch Biochem. Biophys. 177, 427–436 (1976).
Baum et al., J. Dent. Res. pp. 1115–1118, Sep. 1977.
Peters et al., Biochem. Genetics, vol. 15, Nos. 9/10, 1977, pp. 925–946.
Katchalski et al., in *The Proteins*, 2nd Ed., vol. II, 1964, pp. 405–406, 577–578, 587, 597.
Renner et al., Oral Surg., vol. 47, No. 4, 1979, pp. 323–328.
Budtz-Jorgensen, JADA 9, 1978, pp. 474–479.
Tarbet, J. Prosthet. Dent., vol. 48, No. 6, 1982, pp. 647–652.
Budtz-Jorgensen, Scand. J. Dent. Res., 82, 1974, pp. 151–190.
Rubin et al., Proc. Soc. Exptl. Biol. Med. 82, 1953, pp. 231–234.
Yphantis et al., J. Bacteriol. 1967, pp. 1509–1515, vol. 94, No. 5.
Gibson et al., Anal. Biochem, 96, 1979, pp. 352–354.
Peters et al., Biochem. Genetics, vol. 15, Nos. 9/10, 1977, pp. 947–962.
Davenport, Brit. Dent. J., 129, 1970, pp. 151–156.
Balekjian et al., Biochem. Biophys. Res. Comm., vol. 50, No. 3, 1973, pp. 676–682.
Budtz-Jorgensen, Acta Odontolog. Scand. 28, 1970, pp. 71–90.
Hay, cited in Chem. Abstracts, vol. 84:2691j., 1976.

*Primary Examiner*—J. R. Brown
*Assistant Examiner*—Jacqueline M. Stone
*Attorney, Agent, or Firm*—Omri M. Behr

[57] ABSTRACT

Polypeptides containing a substantial proportion of L-histidine are effective fungicidal agents. They are particularly effective against *C. albicans* and have a high degree of safety and nontoxicity because of their structural similarity to naturally occuring histidine-rich polypeptides which are unique to the salivas of humans and old world monkeys.

11 Claims, 4 Drawing Figures

FUNGICIDAL POLYPEPTIDE COMPOSITIONS CONTAINING L-HISTIDINE AND METHODS FOR USE THEREFORE

RELATED APPLICATIONS

This application is a continuation-in-part of our co-pending application, Ser. No. 566515, filed Dec. 29, 1983, now abandoned.

BACKGROUND OF THE INVENTION

Fungal infections of mucosal tissue are particularly troublesome because of the difficulty of effective administration of fungistatic or fungicidal agents, since systemic administration of such agents is not desirable and usually not effective. On the other hand, because of the normal fluid excretion from the mucosa there is a substantial tendency of these fluid excretions to wash out topically administered thereapeutic agents giving rise to the need for either high levels of administration which may lead to undesirable side effects or frequent administration which is not always possible and not alwasy adhered to by the patient. It is therefore desirable to seek fungistatic and fungicidal agents which when used in effective dosages overcome these problems.

There are three areas of concern to physicians and dentists, all involving a different problem of fungal infection. Under normal circumstances fungal infection of the oral cavity is not a problem since salivary clearance and oral hygiene, on a regular basis will not permit fungal infections to take hold. A major and important exception to this situation occurs among denture wearers. In 1956, Fisher (*J. Prosthet. Dent.*, 6, 593 (1956) proposed that a connection might exist between poor denture hygiene and denture stomatitis. This relationship was demonstrated by Budtz-Jorgensen and Bertram (*Acta. Ondontol. Scand.*, 28, 71 (1970). Further work by Budtz-Jorgensen (*J.A.D.A.*, 96, 474 (1978)), showed that *Candida albicans* and related species play a major role in initiating, maintaining and aggravating the disease. He found, for example, that denture stomatitis is present in about 65% of the wearers of complete dentures in the Danish community. This work was confirmed by Tarbet in a United States study (*J. Prothet. Dent.*, 48, 647 (1982)).

A recent survey of this problem was published by Budtz-Jorgensen as a review (*Scand. J. Dent. Res.*, 82, 151-190) (1974)). In his review (at page 174), Budtz-Jorgensen discusses host defense mechanisms in Candida induced denture stomatitis and indicates that certain substances in saliva, for example, lysozyme, act to retard the growth of bacteria and fungi. However, he states (at page 175) that dentures prevent salivary anticandidal substances from getting into contact with and combatting the flora propagating on the palatal mucosal surface. It has been suggested that *C. albicans* must be eliminated from the acrylic surface of the denture itself in order to halt the disease process (Davenport, *Br. Dent. J.*, 129, 151 (1970)). These factors are critical to the design of antifungal agents for denture wearers since they must not only be active but also they must be effectively delivered and/or localized at the interface between the denture and the gum.

It has been previously reported that cationic histidine-rich polypeptides are present in human parotid saliva (Balekjian, *Biochem. Biophys. Res. Com.*, 50, 676 (1973); Baum, et al., *Arch. Biochem. Biophys.*, 177, 427 (1976); Peters and Azen, *Biochem. Genet.*, 15, 925 (1977); and Peters, et al., *Biochem. Genet.*, 15, 947 (1977). Azen (*Biochem. Genet.*, 16, 79 (1978) however states that "he was unable to show biological or functional activity or toxicity of the purified salivary histidine-rich polypeptides. Studies include bacteriostatic, bacteriocidal or opsonizing effects against selected grampositive and gram-negative organisms in culture, the binding of mycoplasma pneumoniae to cell surfaces in culture, enzymatic activity, inhibitory effects against DNA and RNA viruses, toxicity or growth disturbances when injected into newborn rats and effects on ciliary function of the salt water shrimp."

While several different histidine-rich polypeptides, (hereinafter HRP) derived from the salivary glands have been reported and some have been partially sequenced (Peters and Azen, *Biochem. Genet.*, 15, 925 (1977); Baum, et al., *Arch. Biochem. Biophys.*, 177, 427 (1976); Baum, et al., *J. Dent. Res.*, 56, 1115 (1977)), pure preparations have not heretofore been provided. Furthermore, to date, a biological role for the HRP has not been documented. As outlined in this application, the HRP as well as poly-L-histidine and synthetic L-histidine peptides, exhibit antimicrobial actions.

Although Yphantis, et al. (*J. Bacteriol.*, 94, 1509 (1967)) have pointed out that *Candida utilis* is sensitive to the cationic polypeptide, poly-L-lysine, which is also antibacterial (Katchalski, et al., *The Proteins* II, p.405, 1964), Poly-L-lysine unfortunately is known to have unacceptable levels of toxicity in mammalian systems (see for example Rubini, et al., *Proc. Soc. Exptl. Biol. Med.*, 82, 231 (1953)).

Other mucosal areas where Candida infections are prevalent are the vaginal and urethral mucosa. At the present time a limited number of antifungal agents are known which are used clinically with a reasonable measure of success, for example, nystatin and clotrimazole. However, since synthetic fungicides exhibit undesirable toxic side-effects, it would be preferable to use either the body's own naturally produced fungicides or agents structurally related to these natural body products. Naturally occurring agents may also serve to rduce the possibility of survival of resistant forms of the fungi. While fungal infection of the female is more common, current therapeutic methods also consider treatment of the male urethral mucosa, thus it would be desirable to provide compounds compatible therewith.

SUMMARY OF THE INVENTION

Certain histidine-rich polypeptides (HRP's) have been purified from human parotid saliva. It has been found that those HRP's having a substantial proportion, i.e., between about 14 and 40 mole & amino acid residues of L-histidine, have antibacterial and antifungal properties, in particular, against *Streptococcus mutans* and *Candida albicans*.

These antifungal properties reside in the chemical structural characteristics of the histidine residue. However, the amino acid, histidine (monomer) does not possess these properties and the lower histidine oligomers have a lower level of effectiveness. Useful properties begin to appear at the tetramer level and the L-histidine heptamer has been shown to be highly effective. Thus, oligomers of say, 4 to 500 units, are desirable. However, the commercially available poly-L-histidine having about 70 units in the sequence is also active and should be considered within the purview of the present invention. While other amino acids may be present in the polypeptide, the levels of lysine and arginine should be held below about 25 mole % each of the polypeptide.

The polypeptides of the present invention are administrable to the loci of infection, in particular, the oral, vaginal and urethral mucosal surfaces. Delivery may be by any conventional means, preferably topical means. In the case of oral administration, this would include dentrifrices, mouthwashes, denture washes or soaks and denture adhesives or cements. Incorporation into polymers associated within the denture, in particular, with the interface of the denture with the gum, should be considered as part of the invention.

Vaginal administration may be by the usual carriers such as douches, foams, creams, and suppositories, the longer lasting forms being preferred.

Urethral administration is preferably by creams which may be of the same or similar formulation to that used for vaginal administration.

DESCRIPTION OF THE PREFERRED EMBODIMENTS

The active components of the present invention are polypeptides which are at least 4 amino acid residues long and which contain at least 14 mole % amino acid residues of L-histidine, the arginine and lysine components should, suitably, not exceed 25 mole % each of the polypeptide. Activity has been found which a tetramer of L-histidine; however, this level is not deemed entirely satisfactory for clinical purposes. A heptamer of L-histidine has been found to yield very satisfactory resuts, as has a commercially available poly-L-histidine of about 70 units.

With respect to the naturally occurring peptides, peptides having as low as 14 mole % residues of L-histidine have been found active, although better results are obtained with those peptides having 20% or greater suitably 24 to 35 mole % residues of L-histidine. While the reasons are not fully understood, it would appear that a peptide of less than 4 units will penetrate the cell membrane of the microbe which it is attacking and be disposed of by the internal enzymes. On the other hand, units exceeding this size will be blocked by the cell membrane and work their microbiocidal effect thereon. Fungi have an outer chitinous wall and a plasma membrane containing sterol. While applicants do not wish to be bound thereto, it is believed that the polypeptides of the present invention must be small enough to penetrate the outer wall, i.e., probably no more than 500 amino acid units in the chain, and contain sufficient histidine to destroy the membrane while adhering to it. It is not essential that there be a predetermined number of sequential L-histidine units provided that the minimum chain length and the minimum percent histidine residue conditions are met.

Poly-L-histidine is a commercially available mixture of histidine chains of various lengths, up to about 70 amino acid units, produced by the polymerization of N-carboxy anhydride of histidine in the presence of a primary or secondary amine.

The histidine oligomers are similarly commercially available and are produced by single unit build-up in accordance with standard peptide synthesis methodologies.

The compositions containing the polypeptides should contain, depending on the nature of the composition, between about 0.01 and 3% by weight of the polypeptide. The modes of administration are those well recognized in the art for treatment or prevention of the bacterial or fungal infections of the mucosa. Thus, for example, there may be provided vaginal creams, suppositories or solutions comprising between 0.2 and 2% by weight of the histidine containing material. Where the infection is an external one, the cream may be gently massaged into the surrounding areas twice daily. When intravaginal use is recommended, approximately 5 grams of the cream should be injected using a conventional applicator high into the vaginal vault once or twice a day with administration continued for about 1 to about 4 weeks. It may be preferred to utilize vaginal suppositories which are similarly inserted high into the vaginal vault once or twice daily and treatment continued for the same period of time.

The histidine peptides may also be incorporated into vaginal douches, however, it should be borne in mind that for the treatment or prevention of vaginal infections continual and frequent administration is desirable, while in most cases douching once or twice daily for from one week to four weeks is usually contraindicated for other reasons.

A conventional denture adhesive paste may be formulated containing from about 12.5 to about 1,500 milligrams of histidine peptide materials per approximately 100 grams of paste if about 2 grams of this paste is applied in the conventional manner to the contact surface of the denture prior to insertion into the mouth. Such application should be made after overnight soaking in the denture cleanser. Denture cleansers may be formulated by the addition of between 6 and 720, suitably about 60 to 240 milligrams of active agent in a tablet of 3 to 3.5 grams. Such a tablet is dissolved in approximately 250 ml. of water yielding, at a concentration of 240 mg. per tablet, approximately 1 milligram per ml. of active material. In the preferred mode of use, the denture after removal from the patient's mouth, is soaked in this cleanser for from about 8 to about 12 hours. It is not necessary, indeed it is preferred, not to rinse the denture prior to insertion.

If desired, in place of utilizing a denture cement, some denture wearers prefer to use a denture adhesive powder which contains between about 12.5 to about 1,500 milligrams per about 100 grams of powder of which from about 1 to about 2 grams are sprinkled onto the gum contact surface of the denture after overnight soaking and prior to insertion into the mouth.

A mouth spray containing between about 2.5 and about 300 milligrams of the histidine peptide material per about 100 ml. of spray may be formulated. This material may be sprayed as an antimicrobial agent in 0.25 to 0.5 ml. aliquots onto the tooth and gingiva surfaces of each quadrant between 1 and 3 times per day. In the case of denture wearers, the spray may be utilized directly on the denture surface prior to daily insertion of the denture.

If desired, a mouthwash formulation may be provided containing between about 25 to about 3,000 milligrams of histidine peptide material per 1,000 ml. of mouthwash and similarly, a toothpaste may be formulated containing between about 25 and 2,000 mg. per about 100 grams of toothpaste.

EXAMPLE I

Isolation and Characterization of HRPs

Figure 1:
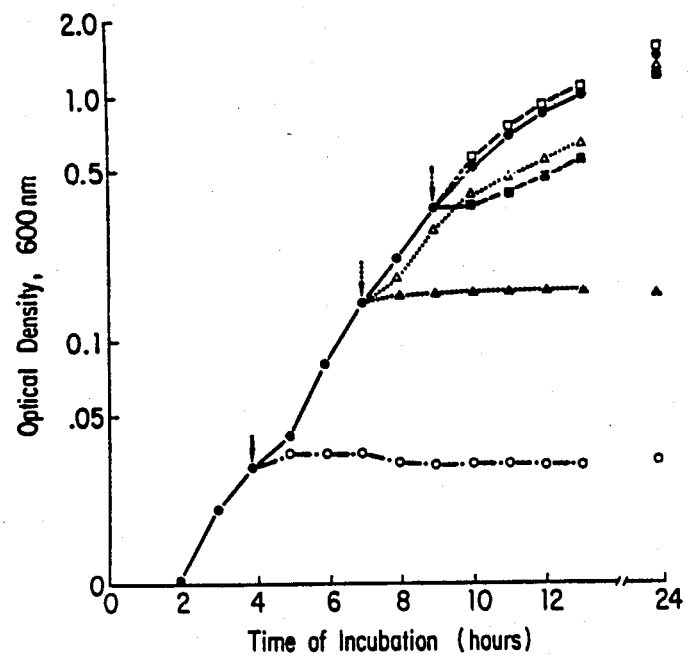
FIG. 1 is a plot showing the effect of the salivary histidine-rich polypeptide on the growth of *C. albicans.*

The HRPs are obtained from the parotid saliva of healthy donors whose salivary flow is stimulated by 2% citric acid or sour lemon drops. An enriched preparation of the HRP free from other salivary components may be isolated by aqueous fractionation on Sephadex G25. A small 280 nm absorption peak which contained a significant amount of 227 nm absorbing material eluted from the column immediately following the voiding peak and prior to the salt peak. This enriched fraction is refractionated on Sephadex G25 to eliminate minor amounts of other salivary components. The individual components of the mixture may be separated either by high performance liquid chromatography (HPLC) (MacKay, et al., *J. Dent. Res.*, Sp. Issue A, 62, 202, Abstr. 291 (1983)) or by cationic polyacrylamide gel electrophoresis (Cationic PAGE) using a modification of the method described by Baum, et al., (*J. Dent. Res.*, 56, 1115 (1977)). Tables 1A, 1B, 2 and 3 provide data on the amino acid compositions of the histidine-rich polypeptides.

TABLE 1A

Amino Acid Composition of Human Parotid HRP Isolated by Sephadex G25 Charomatography.[a]

| Amino Acid | Residues per 100 Residues |
|---|---|
| Asp | 8.6 |
| Thr | 0 |
| Ser | 8.6 |
| Glu | 7.8 |
| Pro | 2.5 |
| Gly | 8.3 |
| Ala | 3.4 |
| Cys | 0 |
| Val | 0 |
| Met | 0 |
| Ile | 0 |
| Leu | 1.1 |
| Tyr | 8.8 |
| Phe | 3.2 |
| Trp | ND[b] |
| His | 24.1 |
| Lys | 13.3 |
| Arg | 10.4 |

[a]Based on the number of amino acid residues per 100 residues recovered from 24-h 6 N HCl hydrolysates. Results express mean of two determinations.
[b]Not determined.

TABLE 1B

Histidine Content of the Human Parotid HRP Determined by Amino Acid Analysis.[b]

| Polypeptide | Percentage of Histidine[b] |
|---|---|
| HRP 1 | 17.8[c] |
| HRP 2 | 13.8[c] |
| HRP 3 | 24.2[c] |
| HRP 4 | 25.2[c] |
| HRP 5 | 33.7[c] |
| HRP 6 | 35.0[c] |
| HRP 6[a], 6[b], 6[c] | 26.5[d] |
| HRP 7 | 26.8[d] |

[a]Individual HRPs were purified from Sephadex G25 preparations by Cationic PAGE or HPLC.
[b]Based on the number of amino acid residues per 100 residues recovered from 24-h 6 N HCl hydrolysates of purified HRPs. Results express the mean of two determinations.
[c]HRP were purified by Cationic PAGE. The individual HRP bands were cut from polyacrylamide slab gels and extracted by the method of Gibson and Gracy (Anal. Biochem., 96, 352 (1979)). Percentage values are based on the total number of amino acid residues recovered. Glycine was excluded from the calculations because a significant amount of glycine is recovered from control polyacrylamide.
[d]HRPs were purified by HPLC. Glycine was excluded from percentage calculations for comparative purposes.

TABLE 2

Amino Acid Compositions of Human Parotid HRP Fractions Purified by HPLC.[a,b]

| Amino Acid | Residues per 100 Residues | | | | |
|---|---|---|---|---|---|
| | HRPs 1,2 | HRPs 3,4 | HRPs 5,6 | HRPs 6[a,b,c] | HRP 7 |
| Asp | 13.6 | 12.5 | 4.9 | 4.2 | 8.3 |
| Thr | 0.0 | 0.0 | 0.0 | 0.0 | 0.0 |
| Ser | 7.1 | 9.2 | 8.0 | 6.7 | 7.5 |
| Glu | 9.3 | 4.6 | 4.7 | 7.0 | 1.9 |
| Pro | 4.3 | Tr | Tr | 0.0 | 0.6 |
| Gly | 10.1 | 7.2 | 8.9 | 8.4 | 10.2 |
| Ala | Tr[c] | 2.1 | 3.2 | 3.5 | 7.7 |
| Cys | 0.0 | 0.0 | 0.0 | 0.0 | 0.0 |
| Val | 0.0 | 0.0 | 0.0 | 0.0 | 0.0 |
| Met | 0.0 | 0.0 | 0.1 | 0.0 | 0.0 |
| Ile | 0.0 | 0.0 | 0.0 | 0.0 | 0.0 |
| Leu | 3.0 | 3.2 | 0.3 | 0.0 | 0.2 |
| Tyr | 12.4 | 11.6 | 8.4 | 2.1 | 0.5 |
| Phe | 9.4 | 3.9 | 3.7 | 4.2 | 0.4 |
| Trp | ND[d] | ND | ND | ND | ND |
| His | 15.9 | 19.8 | 27.8 | 24.3 | 24.1 |
| Lys | 6.9 | 11.9 | 15.3 | 16.8 | 21.6 |
| Arg | 8.2 | 14.1 | 14.2 | 10.3 | 17.0 |

[a]HRP fractions were purified from Sephadex G25 preparations.
[b]Based on the number of amino acid residues per 100 residues recovered from 24-h 6 N HCl hydrolysates. Results express mean of two determinations.
[c]Trace.
[d]Not determined.

TABLE 3

Amino Acid Compositions of the Human Parotid HRP Purified by Cationic PAGE.[a,b]

| Amino Acid | Residues per 100 Residues | | | |
|---|---|---|---|---|
| | HRP 3 | HRP 4 | HRP 5 | HRP 6 |
| Asp | 15.8 | 14.1 | 6.0 | 3.1 |
| Thr | 0.0 | 0.0 | 0.0 | 0.0 |
| Ser | 11.7 | 10.2 | 10.4 | 8.7 |
| Glu | 4.8 | 5.0 | 5.5 | 7.1 |
| Pro | Tr[c] | Tr | 0.0 | 0.0 |
| Gly | ND | ND | ND | ND |
| Ala | 2.8 | 1.9 | 4.1 | 2.0 |
| Cys | 0.0 | 0.0 | 0.0 | 0.0 |
| Val | 0.0 | 0.0 | 0.0 | 0.0 |
| Met | 0.0 | 0.0 | 0.0 | 0.0 |
| Ile | 0.0 | 0.0 | 0.0 | 0.0 |
| Leu | 3.2 | 3.6 | 0.0 | 0.0 |
| Tyr | 7.6 | 6.7 | 2.4 | 3.0 |
| Phe | 3.4 | 4.0 | 4.7 | 5.1 |
| Trp | ND | ND | ND | ND |
| His | 24.2 | 25.2 | 33.7 | 35.0 |
| Lys | 11.8 | 13.4 | 17.4 | 19.1 |
| Arg | 14.8 | 15.7 | 15.9 | 16.8 |

[a]Individual HRPs were purified from Sephadex G25 preparations by Cationic PAGE.
[b]Based on the number of amino acid residues per 100 residues recovered from 24-h hydrolysates. Results express mean of two determinations.
[c]Trace.
[d]Not determined.

EXAMPLE II

Biological Properties of the HRP and Poly-L-Histidine*

Table 4 demonstrates that at concentrations of 25 ug of mixture HRP 1-7 per ml or higher in the yeast synthetic media, there was virtually complete inhibition of growth after a 24 hour incubation period. At 10 µg HRP per ml, a slight inhibition was noted. When HRP was not placed in the growth medium initially but was added to growing cells, the following observations were noted (FIG. 1). (i) The inhibitory effect on growth was greatest at lower cell densities, (ii) the higher the cell density, the greater the concentration required to inhibit growth, (iii) complete growth inhibition could be obtained for 24 hours at cell densities of approximately $10^6$ colony forming units per ml ((optical density 600 nm of 0.2) using an HRP concentration of 250 µg per ml (FIG. 1), (iv) inhibition of growth at this cell concentration ($10^6$ colony forming units per ml) by 50 µg per ml was delayed and was not complete as cells reached optical densities of the control after a 24 hour period, and (v) at still higher cell densities, there was no inhibition of growth at 50 µg HRP per ml but there was the delay in growth at 250 µg HRP per ml. Poly-L-histidine was found to be similarly effective to the HRP (data not shown).

*The term Poly-L-Histidine is used in the experimental section of this specification designating a commercially available product containing homopolymers of L-histidine up to 70 amino acid units in length.

Figure 2:
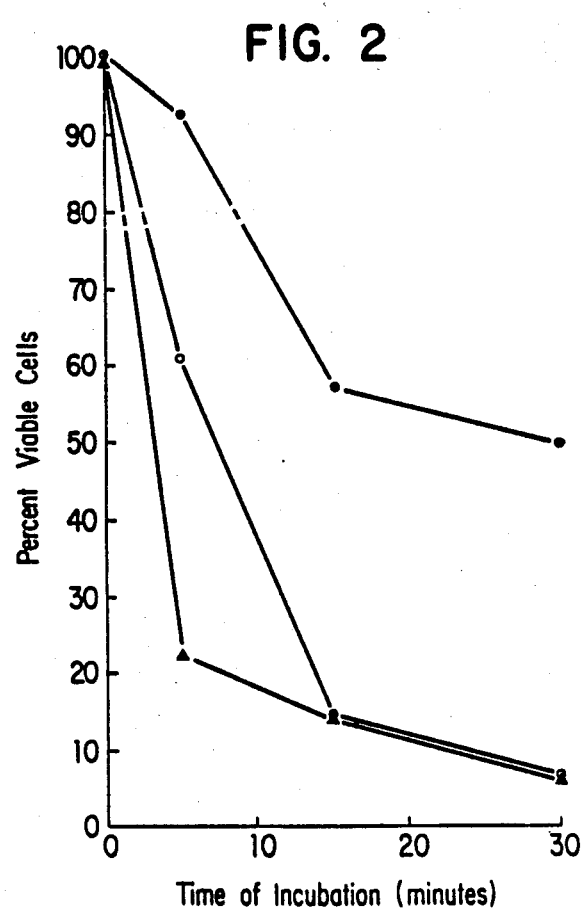
FIG. 2 is a plot showing the effect of the salivary histidine-rich polypeptides on the viability of three strains of *C. albicans* under non-growing conditions.

Under growing conditions, loss of viability of *C. albicans* 18804 correlated with inhibition of growth (Table 4). At concentrations of 25 µg HRP per ml of higher, greater than 99% killing of the yeast was observed when cells were plated ater a period of 24 hours in the growth media. Under non-growing conditions, greater than 90% inhibition of viability of *C. albicans* 18804 was noted with the tested concentration of 100 µg pr ml HRP after a period of 30 min. (Table 5). Compared to *C. albicans* 18804, *C. albicans* 28517 was more sensitive while *C. albicans* 28815 was considerably more resistant under these experimental conditions (FIG. 2).

TABLE 4

Effect of the Histidine-Rich Polypeptides on the Growth and Viability of *Candida Albicans* 18804

| HRP Concn. (ug/ml) | O.D. 600 nm[a] | CFU[b] | Percent Loss of Viability[c] |
|---|---|---|---|
| 0 (Control) | 1.4 | $10^7$ | — |
| 5 | 1.4 | $10^7$ | 0 |
| 10 | 1.2 | $10^7$ | 0 |
| 25 | 0.035 | $14 \times 10^3$ | 99.86 |
| 50 | 0.018 | $73.6 \times 10^2$ | 99.93 |
| 75 | 0.013 | $12.4 \times 10^3$ | 99.88 |
| 100 | 0.01 | $73.6 \times 10^2$ | 99.93 |
| 150 | 0.01 | $5.3 \times 10^2$ | 99.95 |
| 250 | 0.005 | $11.1 \times 10^2$ | 99.99 |

[a]The optical density at 600 nm was measured after 24 hours growth at 37° C. in the yeast synthetic media.
[b]Colony-forming units per ml were determined after plating aliquots from 24 hour growth cultures onto yeast morphology agar for an additional 48 hours at 37° C.
[c]Expressed as a percentage of the control.

TABLE 5

Effect of the Histidine-Rich Polypeptides on the Viability of *Candida albicans* 18804 under Non-Growing Conditions

| Incub. Time (min)[a] | CFU[b] Control × $10^5$ | CFU[b] HRP Exposed[b] × $10^4$ | % Loss of Viability[c] |
|---|---|---|---|
| 0 | 9.6 ± 1.3 | 114 ± 10 | — |
| 5 | 9.0 ± 1.4 | 54 ± 6 | 39.9 |
| 15 | 12.9 ± 1.6 | 18.1 ± 3.5 | 85.9 |
| 30 | 11.4 ± 2.4 | 8.0 ± 0.9 | 93.0 |

[a]Cells with or without a final concentration of 100 µg per ml HRP were suspended in 0.025 MES buffer, pH 5.2. Aliquots were withdrawn at the indicated times and were plated onto yeast morphology agar.
[b]Colony-forming units per ml were determined in duplicate after 48 hours incubation at 37° C.
[c]Expressed as a percentage of the control.

The effects of the HRP on *Streptococcus mutans* are shown in Table 6. The results clearly demonstrate the bacteriocidal activity of both the HRP and hen egg white lysozyme (HEWL) for *S. mutans* SB. After 1 or 2 hours preincubation in MES buffer, pH 5.2, with these molecules, bacterial growth was inhibited progressively after 24 hours with increasing HRP concentrations and with a fixed concentration of HEWL. For the HRP, this 24 hour bacteriostatic effect correlated with a loss of colony forming units and was dependent on HRP concentration (Table 6). At 50 µg HRP per ml (Table 6) in the preincubation mixture corresponding to a final concentration of 1 µg HRP per ml in the growth media, approximately 80% of the cells lost their viability. At 250 µg HRP per ml (Table 6), complete loss of viability was observed under the experimental conditions. After further incubation to a period of 48 hours in the growth media, all cells previously exposed to either HRP or HEWL for 1 hour in the MES buffer attained optical densities similar to the controls. However, with a 2 hour exposure to the MES buffer, those cells showing zero turbidity after the 48 hour period of growth and again did not undergo cell division on solid media (Table 6). The 2 hour preincubation in the MES also permitted lysozyme to continue to be bacteriocidal after 48 hours of incubation. Both the HRP and lysozyme exhibited these effects independent of whether or not Todd Hewitt dialysate was used at neutral or acidic pH (data not shown).

When *S. mutans* GS5 was tested with the HRP, similar effects were noted. Pre-exposure in the MES buffer to 250 ug HRP per ml led to complete inhibition of cell division demonstrating the bacteriocidal effects of the HRP for this *S. mutans* strain (data not shown).

TABLE 6

Effect of HRP Concentration and Preincubation in Acidic Buffer on the Growth and Viability of *S. mutans* SB

| HRP Conc. (µg/ml)[a] | O.D. 675 nm[b] | GFU[c] | % Loss of Viability |
|---|---|---|---|
| 1 Hour Preincubation | | | |
| 0 (Control) | 0.55 (2.0) | $11.4 \times 10^{10}$ | — |
| 25 | 0.48 (2.0) | $8.9 \times 10^{10}$ | 22 |
| 50 | 0.22 (2.0) | $27.5 \times 10^9$ | 76 |
| 100 | 0.05 (2.0) | $9.5 \times 10^9$ | 92 |
| 250 | 0.015 (2.0) | $41.0 \times 10^7$ | 99.6 |
| 500 | 0.015 (2.0) | $30.5 \times 10^7$ | 99.7 |
| 500 (HEWL) | 0.08 (2.0) | $35.5 \times 10^9$ | 69.0 |
| 2 Hours Preincubation | | | |
| 0 (Control) | 0.16 (2.0) | $10.2 \times 10^9$ | — |
| 25 | 0.03 (2.0) | $8.9 \times 10^9$ | 13 |
| 50 | 0.01 (2.0) | $19.0 \times 10^8$ | 81.4 |

TABLE 6-continued

Effect of HRP Concentration and Preincubation in Acidic Buffer on the Growth and Viability of *S. mutans* SB

| HRP Conc. ($\mu g/ml$)[a] | O.D. 675 nm[b] | GFU[c] | % Loss of Viability |
|---|---|---|---|
| 100 | 0.01 (2.0) | $23.5 \times 10^8$ | 77 |
| 250 | 0 (0) | 0 (0) | 100 (100) |
| 500 | 0 (0) | 0 (0) | 100 (100) |
| 500 (HEWL) | 0 (0) | 0 (0) | 100 (100) |

[a]*S. mutans* SB at $5 \times 10^5$ colony forming units per ml was suspended and preincubated in MES buffer, pH 5.2, at an ionic strength of 0.025 for 1 and 2 hours at 37° C. Preincubation included various concentrations of HRP or 500 $\mu$g HEWL per ml and was followed by 50 fold dilution into Todd Hewitt dialysis growth media.
[b]Optical densities were measured after 24 hours and 48 hours (values in parenthesis) incubation at 37° C. for both 1 and 2 hour preincubations.
[c]Colony forming units were determined in duplicate after 24 hours for both 1 and 2 hour preincubations. They were also determined after 48 hours on those 2 hour preincubation samples showing zero density (values in parenthesis).

EXAMPLE III

Studies with HRP 7

(a) Purification

HRP 7 was purified from the mixture of HRP, isolation by Sephadex G25 chromatography, by high performance liquid chromatography. The mixture of the HRP was applied to a $\mu$ Bondapak $C^{18}$ Reverse Phase Column. Initial elution was carried out for 15 minutes with distilled water containing 0.1% trifluoroacetic acid. This was followed first by a 15 minute linear gradient to 15% aqueous methanol containing 0.1% trifluoroacetic acid, then by a 90 minute linear gradient to 50% aqueous methanol containing 0.1% trifluoroacetic acid, and finally by an isocratic 60 minute elution with 50% aqueous methanol containing 0.1% trifluoroacetic acid.

(b) Characterization

HRP 7 is eluted as a single peak in the initial trifluoroacetic acid elution off the high pressure liquid chromatographic column as shown by cationic polyacrylamide gel electrophoresis (data not shown). The amino acid composition is listed above (see Table 2). Based on amino acid analysis, the minimum molecular weight of HRP 7 was calculated to be approximately 7,500 daltons.

(c) Inhibition of Growth of *C. albicans* 18804

Figure 3:
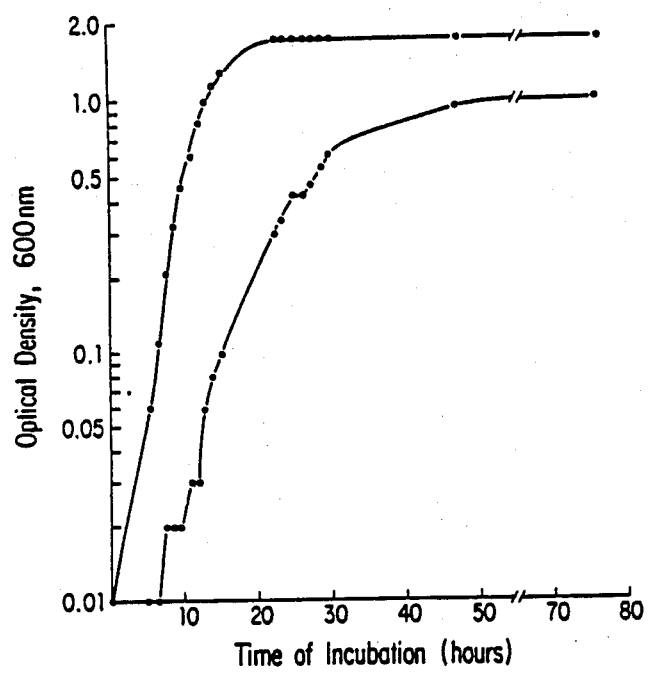
FIG. 3 is a plot of culture optical density against incubation time showing effect of HRP 7 on the growth of *C. albicans*.

A lyophilized culture of *C. albicans* 18804 was inoculated at 37° C. into yeast synthetic medium (YSM) and at the late log phase of growth (optical density 600 nm=0.95), a second transfer into fresh YSM was made overnight. Next morning late log phase cultures were harvested by centrifugation, washed twice in sterile distilled water and then suspended in sterile 0.025M MES buffer, pH 5.3, to an optical density 600 nm=0.20 (106 colony forming units per ml). From this suspension, 0.1 ml aliquots were transferred to $13 \times 100$ mm screw cap tubes containing 2.5 ml of YSM without (controls) or with HRP 7. Based on optical density 227 nm absorption, NRP 7 was used at a final concentration of 80 $\mu$g per ml. However, it should be noted that HRP 7 may be more active than depicted below. The purified material isolated by high performance liquid chromatography was in the trifluoroacetate form which may inhibit the binding of the histidine peptide to the negatively-charged fungal cell membrane. No attempt was made to change the counter anion on the peptide. Nevertheless, there was significant inhibition as noted in FIG. 3.

EXAMPLE IV

Effects of Synthetic Oligomers of His-7 and His-4 on Candida Albicans 18804

His-7, containing seven residues of L-histidine, was a custom synthesis request from Peninsula Laboratories, Belmont, Calif. The material was purified to homogeneity. Unpurified His-4, containing four residues of L-histidine, was also obtained from Peninsula Laboratories. Both peptides were solubilized in 5 parts of 0.001 M acetic acid and 3.5 parts of 0.025 M MES buffer, pH 5.3. The solutions were filter sterilized through Swinney 0.2 micron GSTF Millipore filters. The final concentration of the peptides were 220 $\mu$g per ml which is considerably lower than the 1.5 mg per ml used in the denture experiments (see below).

A lyophilized culture of *C. albicans* was inoculated at 37° C. into yeast synthetic medium (YSM) and at the late log phase of growth (optical density 600 nm 0.95), a second transfer into fresh YSM was made overnight. Next morning, late log phase cultures were harvested by centrifugation, washed twice in sterile distilled water and then suspended in sterile 0.025 M MES buffer, pH 5.3, to an optical density 600 nm=0.20 ($10^6$ colony forming units per ml). From this suspension, 0.1 ml aliquots were transferred to $13 \times 100$ mm screw cap tubes containing 2.5 ml of YSM without (Controls) or with 220 $\mu$g per ml of either His-4 or His-7. The growth curve was then followed by measuring the increase in turbidity at 600 nm.

Figure 4:
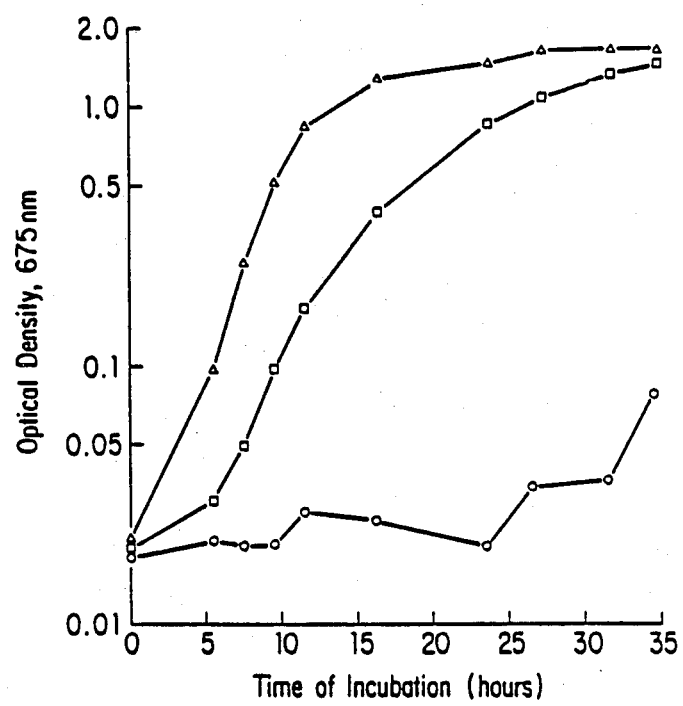
FIG. 4 is a plot of culture optical density against incubation time showing effect of tetra-L-histidine and hepta-L-histidine on the growth of *C. albicans*.

FIG. 4 demonstrates that His-7 shows a marked effect on the growth of *C. albicans* 18804 in suspension culture. After 35 hours of incubation, cells are just beginning to divide. In contrast, His-4 does effect growth but much less than His-7.

EXAMPLE V

In Vitro Experiments Employing Denture Acrylic Strips

Denture acrylic was uniformly cut into strips of dimension ⅛ inches × ⅛ inches × 3½ inches. Each strip was attached to the inside of the cap of the screw cap tube (13 × 100 mm) such that the bottom of each strip lay ⅜ inches from the bottom of each tube. Tubes containing denture strips were sterilized in the ethylene oxide sterilizer.

(a) Effects of the Synthetic Peptide of Seven Residues of L-Histidine (His-7) on the Proliferation of *Candida albicans* 18804 on Denture Acrylic Strips A concentration of 3 mg/ml of His-7 was prepared by solubilizing 25.5 mg of His-7 in a total volume of 8.5 ml consisting of 5 ml of 0.0001 M acetic acid and 3.5 ml of 0.025 M MES buffer, pH 5.3. The final pH of the solution was 6.0 due to the basic nature of His-7. The solution was sterilized through a Swinney 0.2 micron GSTF Millipore filter.

A lyophilized culture of *C. albicans* was inoculated at 37° C. into yeast synthetic medium (YSM) and at the late log phase of growth (optical density 600 nm=0.95), a second transfer into fresh YSM was made overnight. Simultaneously, denture acrylic strips were placed overnight at room temperature into tubes containing only MES buffer. Next day, the precoated denture strips were transferred to tubes containing 2.5 ml of the grown up *C. albicans* (optical density 600 nm=1.0, corresponding to about $10^7$ colony forming units per ml). After 2.25 hours, the control strip was placed into YSM while His-7 precoated strips were placed into YSM containing 1.5 mg per His-7. Tubes were incubated at 37° C. for approximately 24 hours.

The control tube was observed to contain *C. albicans* in the media indicating that cells had proliferated on the strip, fallen off and multiplied in the media. The optical density 600 nm read 1.2 after 24 hours incubation. However, there was no growth in the YSM media containing His-7 indicating that His-7 must be affecting proliferation on the denture strip and/or stopping growth of any organisms that fall off into the media.

Both the control tube and the His-7 tubes were then transferred to fresh YSM without any His-7. Tubes were incubated at 37° C. and the growth curve was monitored by the increase in optical density at 600 nm.

TABLE 7

Effect of His-7 on Growth of *Candida albicans* with Pretreatment of Denture Strips

| Sample | Optical Density at 600 nm Hours of Incubation | | | | | |
|---|---|---|---|---|---|---|
| | 0 | 9 | 13 | 15 | 27 | 34 |
| Control Strip | .01 | .30 | .72 | .98 | 1.5 | 1.75 |
| His-7 strip | .01 | .01 | .02 | .02 | .09 | .50 |
| His-7 strip | .02 | .02 | .03 | .02 | .03 | .05 |

The results shown in Table 7 indicate that either the precoating or the incubation or both with His-7 results in a significant delay in growth at least for 24 hours. Such inhibition would be ideal for the denture patient where the number of Candida could be kept under control.

(b) Effects of Poly-L-Histidine on the Proliferation of *Candida albicans* 18804 on Denture Acrylic Strips Poly-L-histidine is commercially available. We purchased our fitst batch from Miles Laboratories, Naperville, Ill. The material is prepared by polymerizing the n-carboxyanhydride of histidine in the presence of a primary or secondary amine. Materials prepared in this manner are heterogeneous in that one obtains a mixture of poly-L-histidine peptides which vary in molecular weight from 5,000 to 15,000 with an average molecular weight of about 10,000.

In this experiment, poly-L-histidine was dissolved in 0.025 M MES buffer, pH 5.2 with heating. As in the previous experiment, denture strips were first pretreated with poly-L-histidine (4 mg per ml) overnight prior to incubation with *Candida albicans* for 2¼ hours. Strips were then transferred to YSM without poly-histidine (controls) or to YSM containing poly-histidine at 2 mg per ml. Although there was precipitation of the poly-L-histidine in the YSM, strips were incubated for 24 hours until controls had reached an optical density at 600 nm=1.2 corresponding to $10^7$ colony-forming units per ml. As in experiment with the L-histidine heptapeptide, strips were then transferred to YSM without poly-L-histidine and the growth curve was followed by monitoring the increase in turbidity.

TABLE 8

Effect of Poly-L-Histidine on the Growth of *Candida albicans* without Pretreatment of Denture Strips

| Sample | Optical Density at 600 nm - Hours of Incubation | | | | | | |
|---|---|---|---|---|---|---|---|
| | 0 | 12 | 15 | 19 | 31 | 60 | 80 |
| Control Strip | .02 | .46 | .80 | 1.20 | 1.75 | 2.0 | 2.0 |
| Control Strip | .02 | .55 | .85 | 1.25 | 1.75 | 2.0 | 2.0 |

TABLE 8-continued

Effect of Poly-L-Histidine on the Growth of *Candida albicans* without Pretreatment of Denture Strips

| Sample | Optical Density at 600 nm - Hours of Incubation | | | | | | |
|---|---|---|---|---|---|---|---|
| | 0 | 12 | 15 | 19 | 31 | 60 | 80 |
| Poly-His Strip | .02 | .04 | .04 | .05 | .05 | .05 | .05 |
| Poly-His Strip | .02 | .03 | .03 | .03 | .03 | .03 | .03 |

Poly-L-Histidine seems to be even more effective than His-7 (compare Table 8 to Table 7). Growth is inhibited for 80 hours.

(c) Effect of L-Histidine Heptapeptide without Precoating of Denture Strips

This experiment was similar to the previous to experiments except that there was no precoating of the denture strips. After incubation of strips in the Candida, a control strip was incubated overnight in the MES-YSM while two additional strips were incubated in MES-YSM containing 1.5 mg per ml of His-7. Strips were then transferred to YSM without additives and the growth curve was followed as outlined previously.

TABLE 9

Effect of His-7 on Growth of *Candida albicans* without Pretreatment of Denture Strips

| Sample | Optical Density at 600 nm - Hours of Incubation | | | | | | |
|---|---|---|---|---|---|---|---|
| | 0 | 7 | 10 | 14.5 | 17.5 | 30 | 36 |
| Control | .01 | .24 | .61 | 1.09 | 1.39 | 1.44 | 1.68 |
| His-7 | .01 | .02 | .01 | .03 | .03 | .03 | .10 |
| His-7 | .01 | .01 | .02 | .06 | .08 | .88 | 1.41 |

Again, notice in Table 9 the variability between strips. On one His-7 strip, all the Candida seem to have been destroyed while on the other His-7 strip, some organisms have survived such that growth is evident after a long period of time. However, virtually no growth is seen at 17.5 hours.

Compared to the results with precoating (see Table 7), the effects are similar although precoating of dentures with His-7 may make some difference in the time delay of growth of the fungus.

Formulations and Methods of Use

The antimicrobial formulations of the present invention are useful against a variety of organisms found in the oral mucosa, the vaginal mucosa and the urethral mucosa. In the oral cavity problems are caused, in particular, although not exclusively, by *Streptococcus mutans* and Candida species, particularly *Candida albicans*. Vaginitis can be caused by *Candida albicans, Trichomonas vaginalis, Haemophilus vaginalis,* and various Steptococci and Staphylococci.

In the oral formulations it is desirable to provide for a pH of about pH 5.5 since the histidine peptides are most effective at this range. The vaginal and urethral formulations should be set at a slightly more acidic pH, namely about 4.5. Although this is not optimal from the point of view of effectiveness of the histidine peptides, higher pH's tend to induce pathogenic growth and therefore should be avoided.

The dental formulations when intended as antibacterials should contain between 25 and 500, suitably 50 to 250 milligrams of the peptides per ml.

For antifungal purposes, a slightly high range is preferable, namely from 25 to 3,000, most suitably 50 to 1,500 milligrams per ml. These formulations apply to the concentrations as they are applied into the mouth.

The vaginal and urethral antibacterial or antifungal agents contain the peptides in between 0.2 to 2% by weight, suitably 0.4 to 1% by weight.

While the invention is in no way considered to be limited thereto, compositions for oral use include toothpaste, mouth sprays, mouthwashes, denture adhesive pastes, denture adhesive powder, denture tablet cleanser and th elike and the vaginal and urethral compositions include creams, suppositories, and vaginal deodorant solutions. Specific formulations for the foregoing, set forth in greater detail hereinbelow, are further illustrative of the nature of the present invention. The compositions are prepared using methods familiar to those skilled in the art. It will be understood that modifications thereof obvious to those skilled in the art are to be included within the spirit and purview of this application and the scope of the appended claims.

EXAMPLE VI

Vaginal Cream

| Ingredients | Percent (w/w) |
|---|---|
| (One of the following) | |
| Salivary Histidine-Rich Polypeptides* | 0.2-2 |
| Poly-L-Histidine | 0.2-2 |
| Synthetic Heptapeptide of L-Histidine | 0.2-2 |
| Cetyl Alcohol | 0.5 |
| Stearic Acid | 25 |
| Sodium Lauryl Sulfate | 0.2 |
| Glycerin | 10 |
| Triethanolamine | 0.2 |
| Methyl Paraben | 0.1 |
| Propyl Paraben | 0.1 |
| Water to Make | 100% |
| pH adjusted to 4.5 | |

*Any of or combinations of the HRPs isolated by the procedures of Example I.

For topical use, gently message cream into the affected and surrounding areas twice daily (morning and evening). For intravaginal use, apply about 5 gm of cream with applicator high into the vaginal vault once or twice daily. Continue as indicated until vaginitis is eliminated (usually one to four weeks).

EXAMPLE VII

Vaginal Suppositories

| Ingredients | Percent (w/w) |
|---|---|
| (One of the following) | |
| Salivary Histidine-Rich Polypeptides* | 0.2-2 |
| Poly-L-Histidine | 0.2-2 |
| Synthetic Heptapeptide of L-Histidine | 0.2-2 |
| Polyethylene Glycol 4000 | 25 |
| Polyethylene Glycol 1000 | 35 |
| Polysorbate 80 | 2 |
| Glycerin | 25 |
| Methyl Paraben | 0.1 |
| Propyl Paraben | 0.1 |
| Water to Make | 100% |
| pH adjusted to 4.5 | |

*Any of or combinations of the HRPs isolated by the procedures of Example I.

Insert one 3 gm suppository into the vaginal vault once or twice daily. Continue as indicated until vaginitis is eliminated (usually one to four weeks).

EXAMPLE VIII

Vaginal Deodorant Solution

| Ingredients | Percent (w/w) |
|---|---|
| One of the following: | |
| Salivary Histidine-Rich Polypeptides* | 0.2-2 |
| Poly-L-Histidine | 0.2-2 |
| Synthetic Heptapeptide of L-Histidine | 0.2-2 |
| Sodium Acetate.3H$_2$O | 0.17 |
| Acetic Acid | 0.07 |
| Sodium Chloride | 0.88 |
| Ethyl Alcohol (95%) | 5.0 |
| Sodium Lauryl Sulfate | 0.5 |
| Menthol | 0.25 |
| Thymol | 0.25 |
| Methyl Salicylate | 0.5 |
| Water to Make | 100% |
| pH adjusted to 4.5 | |

*Any of or combinations of the HRPs isolated by the procedures of Example I.

Apply about 200 ml daily to vaginal mucosal surfaces.

EXAMPLE IX

Denture Adhesive Paste

One of the following:

| | |
|---|---|
| Salivary Histidine-Rich Polypeptides* | 0.0125-1.5 gm |
| Poly-L-Histidine | 0.0125-1.5 gm |
| Synthetic Heptapeptide of L-Histidine | 0.0125-1.5 gm |
| Carboxymethylcellulose Gum | 32 gm |
| Pluronic F107 (BASF Wyandotte Corp.) | 13 gm |
| Petrolatum | 42 gm |
| Liquid Petrolatum | 12 gm |
| Propyl Paraben | 0.1 gm |
| Flavor** | 0.05 gm |
| Adjust pH to 5.5 | |

*Any of or combinations of the HRPs isolated by the procedures of Example I.
**Examples of suitable flavoring constituents are flavoring oils, e.g., oils of spearment, pepermint, wintergreen, sassafras, clove, sage, eucalyptus, marjoram, cinnamon, lemon, orange and methylsalicylate.

Apply paste to denture after overnight soaking in denture cleanser. Rinse denture with water and apply a thin film of paste (approximately 2 gm) onto the surface of each denture and insert into the mouth.

EXAMPLE X

Denture Adhesive Powder

One of the following:

| | |
|---|---|
| Salivary Histidine-Rich Polypeptides* | 0.0125-1.5 gm |
| Poly-L-Histidine | 0.0125-1.5 gm |
| Synthetic Heptapeptide of L-Histidine | 0.0125-1.5 gm |
| Karaya Gum | 94.6 gm |
| Pluronic F108 (BASF Wyandotte Corp.) | 4.9 gm |
| Calcium Silicate | 0.1 gm |
| Flavor** | 0.4 gm |
| Adjust pH to 5.5. | |

*Any of or combination of the HRPs isolated by the procedures of Example I.
**Examples of suitable flavoring constituents are flavoring oils, e.g., oils of spearment, pepermint, wintergreen, sassafras, clove, sage, eucalyptus, marjoram, cinnamon, lemon, orange and methylsalicylate.

Apply powder to denture aftr overnight soaking in denture cleanser. Rinse denture with water and sprinkle antimicrobial powder (approximately 1 to 2 gm) onto the surface of each denture and insert into the mouth.

EXAMPLE XI

| Denture Tablet Cleanser | Each Tablet |
|---|---|
| One of the following: | |
| Salivary Histidine-Rich Polypeptides* | 6–720 mg |
| Poly-L-Histidine | 6–720 mg |
| Synthetic Heptapeptide of L-Histidine | 6–720 mg |
| Potassium Monopersulfate | 960 mg |
| Sodium Borate Perhydrate | 480 mg |
| Sodium Bicarbonate | 1116 mg |
| Citric Acid | 362 mg |
| Sodium Carbonate | 32 mg |
| Magnesium Stearate | 18 mg |
| Sodium Lauryl Sulfate | 20 mg |
| Peppermint Oil | 2 gm |
| Silica | 14 mg |
| Adjust pH to 5.5 | |

*Any of or combination of the HRPs isolated by the procedures of Example I.

Dissolve each tablet in one denture cup (approximately 8 ounces) of water. Soak denture in antimicrobial denture cleanser overnight. Rinse denture with water prior to reinsertion into the mouth.

EXAMPLE XII

Mouth Spray

One of the following:

| | |
|---|---|
| Salivary Histidine-Rich Polypeptides* | 0.0075–0.9 gm |
| Poly-L-Histidine | 0.0075–0.9 gm |
| Synthetic Heptapeptide of L-Histidine | 0.0075–0.9 gm |
| Peppermint Spirit | 43.2 gm |
| Saccharin Sodium | 0.07 gm |
| Sodium bicarbonate | 0.25–3.24 gm |
| Sodium chloride | 0.23–1.76 gm |
| Sodium thiocyanate | 0.49–2.4 gm |
| Water to | 300 gm |
| Adjust pH to 5.5 | |

*Any of or combination of the HRPs isolated by the procedures of Example I.

The formulation is utilized as an antibacterial mixture by spraying aliquots of 0.25 to 0.50 ml onto the gingiva and tooth surface of each quadrant between 1 and 3 times a day. For denture stomatitis, apply similar quantities of the spray directly to the denture as an antifungal mixture after overnight soaking in the denture and prior to reinsertion into the mouth.

EXAMPLE XIII

Mouthwash Formulation

One of the following:

| | |
|---|---|
| Salivary Histidine-Rich Polypeptides* | 0.025–3.0 gm |
| Poly-L-Histidine | 0.025–3.0 gm |
| Synthetic Heptapeptide of L-Histidine | 0.025–3.0 gm |
| Thymol | 0.5 gm |
| Eucalyptol | 1.0 gm |
| Methyl Salicylate | 0.5 gm |
| Ethyl Alcohol (95%) | 100.0 gm |
| Glycerin | 100.0 gm |
| Water to make | 1000.0 gm |
| Adjust to pH 5.5 | |

*Any of or combination of the HRPs isolated by the procedures of Example I.

The formulation is utilized as an antibacterial or antifungal mixture by rinsing the mouth for about 30–60 seconds from 1–3 times per day with 10 to 15 ml of undiluted wash.

EXAMPLE XIV

Toothpaste (Gel Formulation)

One of the following:

| | |
|---|---|
| Salivary Histidine-Rich Polypeptides* | 0.025–2.0 gm |
| Poly-L-Histidine | 0.025–2.0 gm |
| Synthetic Heptapeptide of L-Histidine | 0.025–2.0 gm |
| Carboxymethyl Celulose | 1.8 gm |
| Carbowax Polyethylene Glycol 600 (Union Carbide Corp.) | 25 gm |
| Zeo-49 (Huber Co.)** | 38 gm |
| Sodium Lauryl Sulfate | 1.5 gm |
| Sodium Saccharin | 0.2 gm |
| Sodium Benzoate | 0.5 gm |
| Flavor*** | 1.0 gm |
| Water to make | 100 gm |
| Adjust to pH 5.5 | |

*Any of or combination of the HRPs isolated by the procedures of Example I.
**Sodium Aluminosilicate.
***Examples of suitable flavoring constituents are flavoring oils, e.g., oils of spearment, pepermint, wintergreen, sassafras, clove, sage, eucalyptus, marjoram, cinnamon, lemon, orange and methylsalicylate.

Product is utilized as an antimicrobial ar antifungal preparation by cleaning teeth with about 1 and 2 gm of gel between 1 and 3 times per day.

We claim:

1. A fungicidal composition effective against *Candida albicans* comprising a pharmaceutically acceptable topical carrier and between 0.0025 and 3% by weight of at least one polypeptide of up to about 500 amino acid units and containing at least 4 amino acid units of L-histidine and 14 mole % of whose amino acid residues are L-histidine, wherein the lysine and arginine content is less than 35.9 mole % each of the total peptide chain.

2. A composition of claim 1 wherein the polypeptide is selected from the group consisting of poly-L-histidine, having from 4 to about 500 amino acid units and polypeptides having the structure of histidine-rich polypeptides derived from human saliva having the characteristics of the peptides of claim 1.

3. A composition according to claim 1 wherein the carrier is a topically administerable carrier.

4. A composition of claim 3 wherein the carrier is a dentifrice, a mouthwash, a mouth spray, a denture wash, or a denture adhesive.

5. A composition of claim 3 wherein the carrier is a vaginal cream, a vaginal deodorant solution or a vaginal suppository.

6. A composition of claim 1 wherein the carrier is a water swellable polymer having the polypeptide incorporated therein.

7. An oral antifungal composition of claim 1 comprising between 25 and 3,000 micrograms per ml of the polypeptide and an orally acceptable carrier therefore.

8. An antivaginitis composition of claim 1 comprising between 0.2 and 2% by weight of the polypeptide in a vaginally acceptable carrier.

9. A method of combatting oral infection caused by *Candida albicans*, in a patient in need thereof which comprises administering to the oral cavity a fungicidally effective amount of a polypeptide of up to 500 amino acid units containing at least 4 amino acid units of L-histidine and containing at least 14 mole % of whose amino acid residues are L-histidine, wherein the lysine and arginine content is less than 35.9 mole % of the total peptide chain.

10. A method of combatting vaginal infection caused by *Candida albicans*, in a patient in need thereof, which comprises administering to the vaginal cavity a fungicidally effective amount of a polypeptide of up to 500 amino acid units containing at least 4 amino acid units of L-histidine and containing at least 14 mole % of whose amino acid residues are L-histidine, wherein the lysine and arginine content is less than 35.9 mole % of the total peptide chain.

11. A method of combatting urethral infection caused by *Candida albicans*, in a patient in need thereof, which comprises administering to the vaginal cavity a fungicidally effective amount of a polypeptide of up to 500 amino acid units containing at least 4 amino acid units of L-histidine and containing at least 14 mole % of whose amino acid residues are L-histidine, wherein the lysine and arginine content is less than 35.9 mole % of the total peptide chain.

* * * * *